United States Patent [19]

Renault

[11] Patent Number: 4,671,286

[45] Date of Patent: Jun. 9, 1987

[54] RF THERAPY APPARATUS

[75] Inventor: Joel E. Renault, Saint-Gregoire, France

[73] Assignee: Compagnie Francaise D'Electronique Medicale International SA (C.O.F.R.E.M. International SA), France

[21] Appl. No.: 585,570

[22] Filed: Mar. 2, 1984

[30] Foreign Application Priority Data

Mar. 4, 1983 [FR] France ............................... 83 03969

[51] Int. Cl.⁴ .............................................. A61N 1/00
[52] U.S. Cl. .................................................... 128/422
[58] Field of Search ................................. 128/422, 804

[56] References Cited

U.S. PATENT DOCUMENTS

| 3,513,851 | 5/1970 | Smith et al. | 128/422 |
| 3,670,737 | 1/1972 | Peard | 128/422 |
| 3,800,802 | 4/1974 | Berry et al. | 128/422 |
| 3,952,751 | 4/1976 | Yarger | 128/422 |
| 4,210,152 | 7/1980 | Berry | 128/422 |
| 4,318,411 | 3/1982 | Elmovist | 128/419 PG |

FOREIGN PATENT DOCUMENTS

| 0058564 | 2/1982 | European Pat. Off. |
| 2097138 | 6/1971 | France |
| 2391738 | 9/1977 | France |
| 2394281 | 6/1978 | France |
| 2440202 | 10/1978 | France |

OTHER PUBLICATIONS

Happell et al, "Engineering Electronics", McGraw-Hill Book Co. Inc., New York, 1953, pp. 117-118 & 139.

Primary Examiner—William E. Kamm
Attorney, Agent, or Firm—Laff, Whitesel, Conte & Saret

[57] ABSTRACT

The apparatus is comprised of an analog portion which generates and shapes a high frequency signal transmitted by a treatment head and a logic portion which generates time segment cuts and regulates the amplitude of the high frequency signal.

The analog part is comprised of, in cascade, a quartz crystal stabilized high frequency oscillator (1), a modulation stage (2), a preamplification stage (3), a power amplification stage (4) and a bandpass filter (5) whose output is connected to the excitation input of the head (6). The logic part (7) generates a train of pulses which are applied to the modulating input of modulator (2) and is comprised of a digital pulse width regulator circuit (10), a pulse repetition rate regulator circuit (9), a pulse amplitude regulator circuit (11) and a continuous or rhythmic operating period regulator circuit.

11 Claims, 13 Drawing Figures

RF THERAPY APPARATUS

The present invention concerns a therapeutic non-thermal instrument and, in particular, its constituent electronic circuits.

Therapeutic non-thermal instruments have been known for approximately forty years. For the purpose of illustration, we can refer to the descriptions of instruments of this type in patents U.S. Pat. Nos. 2,448,541, 3,503,403, 3,515,851, French-No. 2,097,138, French-No. 2,291,773, French-No. 2,301,965.

All the therapeutic non-thermal instruments comprise a high frequency oscillator feeding a signal input of a modulator whose control input is connected to a pulse generator and whose output is connected to a treatment head by a transformer. Amplifiers are connected in this circuit to maintain adequate levels.

Originally, the oscillator, the modulator and the pulse generator were electronic circuits using tubes. However, as technology evolved, these circuits have become progressively transistorized, with the exception of the power stages in which tubes were retained. It was then necessary in these instruments to provide two power supplies.

One object of the invention consists in providing a completely transistorized therapeutic instrument.

In accordance with a characteristic of the invention, an instrument is provided comprised of an analog part which generates and shapes the high frequency signal transmitted by the treatment head and a logic part to generate time segment cuts and to regulate the peak amplitude of the high frequency signal, the analog part comprising, in cascade, a high frequency quartz stabilized osillator, a modulation stage, a preamplification stage, a power amplification stage and a bandpass filter whose output is connected to the excitation input of the head, the logic part generating a train of impulses which are applied to the modulation input of the modulator and is comprised of a digital circuit to regulate the duration of the impulses, a digital circuit to regulate the frequency of the impulses, a circuit to regulate the amplitude of the impulses and a circuit to regulate the continuous or rhythmical operation of the instrument.

In accordance with another characteristic, the modulator is a transistor amplifier operating in class C and tuned to the same frequency as the high frequency oscillator, the supply voltage of the amplifier being determined by the output signal of the logic part applying the train of impulses.

The characteristics of the above mentioned invention, as well as others, will become clearer upon reading the description of an embodiment, the said description being carried out with respect to the attached drawings, among which.

Figure 1:
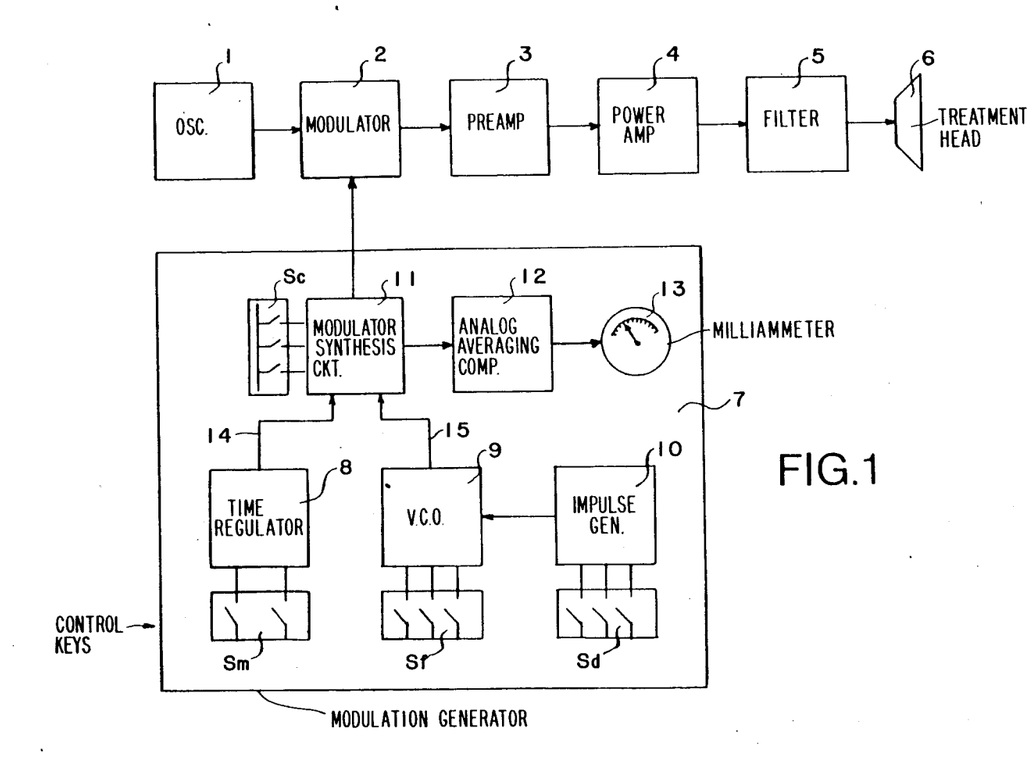
FIG. 1 is a block diagram of a therapeutic instrument.

The therapeutic instrument of FIG. 1 is comprised of a high frequency signal generation and processing analog portion and a logic portion to generate time segment splicing and amplitude regulation signals.

The high frequency analog part comprises an oscillator 1 whose output is connected to the high frequency input of a modulator 2 whose modulated signal output is connected to the input of a preamplifier 3 whose output is connected to the input of a power amplifier 4 whose output is connected to the input of a filter 5 whose output is connected to a treatment head 6.

The modulation input of modulator 2 is connected to the output of a modulating signal generator 7.

The generator 7, which makes up the logic part of the instrument, drives the treatment head 6 via an open-loop circuit without feedback, the generator is comprised of an operating time regulation circuit 8 that can be set by control keys Sm and whose output is connected by a link 14 to an input of a modulation synthesis circuit 11. The generator 7 also is comprised of an impulse generator 10 associated with a set of keys Sd to regulate the width of the impulses. The output of pulse generator 10 is connected to the modulating input of a voltage controlled oscillator 9 whose frequency can be regulated through a set of keys Sp. The pulsed output of oscillator 9 is connected, by a link 15 to a second input of the synthesizer circuit 11. The synthesizer circuit 11 is associated with a set of keys Sc and has its output connected, on one hand, to the modulation input of modulator 2, and on the other hand to an analog averaging computer 12 whose output is connected to a milliammeter type of measuring instrument 13.

The oscillator 1 is a transistor quartz stabilized frequency oscillator. The quartz crystal has been selected such that the operating frequency for the embodiment is at 27.125 MHz in the HF band. The oscillator itself is followed by a fixed gain frequency selective transistor amplifier.

The modulator 2 is a transistor amplifier whose supply voltage is controlled by the voltage applied to the modulation input. In practice, its supply voltage is null, which ensures that the transistor is cut off or equal to a voltage Vi which defines the peak signal power generated by the modulator.

The preamplifier 3 is a transistor amplifier charged by a balancing transformer.

The power amplifier 4 is a push-pull type amplifier charged by a symmetric-assymetric transformer.

The filter 5 and the treatment head 6 can be of conventional design.

Figure 2:
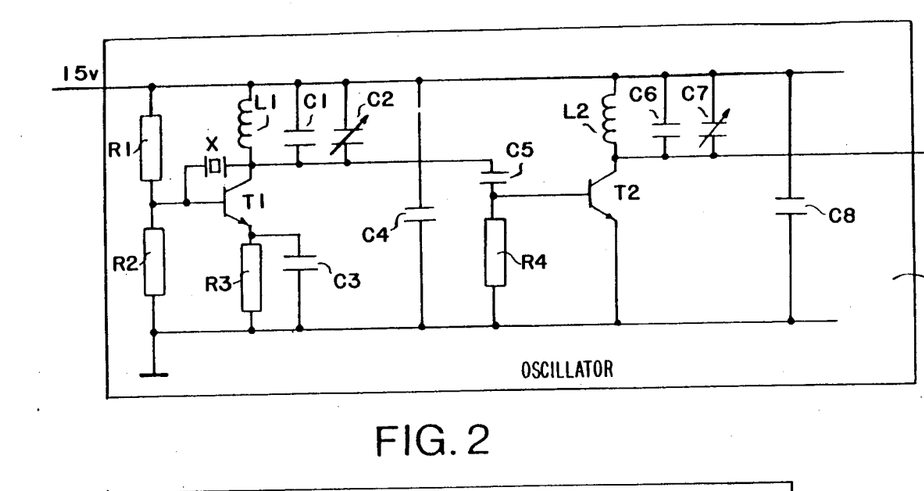
FIG. 2 is the schematic of a high frequency oscillator.

The oscillator 1 in FIG. 2 is comprised of an NPN transistor T1 whose base is connected to a quartz crystal resonating at 27.125 MHz and thus defining the oscillating frequency. The base is connected at a common point to two resistors R1 and R2 connected in series between the 15 V supply and ground. The voltage divider made up by resistors R1 and R2 provides a voltage of 4.8 V to the base of the transistor. The collector of transistor T1 is connected to the 15 V supply by a parallel circuit comprised of an inductor L1, a fixed capacitor C1 and a variable capacitor C2. The values of L1, C1 and C2 are selected such that the set up oscillates at the quartz crystal frequency of 27.125 MHz. The emitter of transistor T1 is connected to ground by a resistor R3 in parallel with a capacitor C3. The biasing voltage of the emitter is set at 4.2 V. Under these biasing conditions, the transistor operates in class A. A capacitor C4 guarantees decoupling between the 15 V supply and ground.

The collector of T1 is connected by a link capacitor C5 to the base of an NPN transistor T2 which constitutes the active component of the fixed gain amplifier. The base of T2 is again connected to ground by a resistor R4, its emitter is connected directly to ground and its collector is connected to the 15 V supply by a parallel circuit comprising an inductor L2, a fixed capacitor C6 and a variable capacitor C7. The bias induced by resistor R4 is such that transistor T2 operates in class C. A capacitor C8 guarantees decoupling between the +15 V supply and ground.

The collector of transistor T2 yields a 27.125 MHz signal supplied by the T1 crystal oscillator and amplified by T2.

Figure 3:
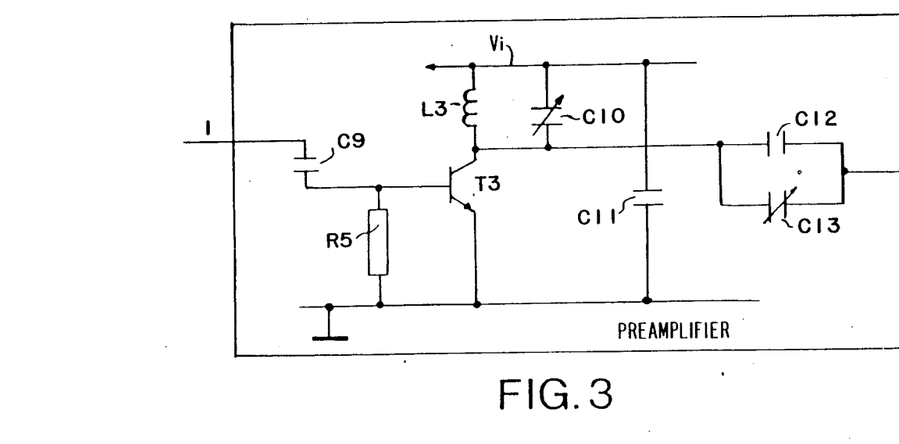
FIG. 3 is the schematic of the modulator.

In the preamplifier 3, FIG. 3, the output of 2, namely the collector of T2, is connected, by a link capacitor C9, to the base of an NPN transistor T3. The base of transistor T3 is connected to ground by a resistor R5, its emitter is connected directly to ground and its collector is connected to a modulated source of voltage Vi by a parallel circuit comprising an inductor L3 and a variable capacitor C10. A capacitor C11 guarantees decoupling between the supply Vi and ground. The bias at the base of transistor T3, provided by resistor R5, is such that transistor T3 operates in class C.

Figure 4:
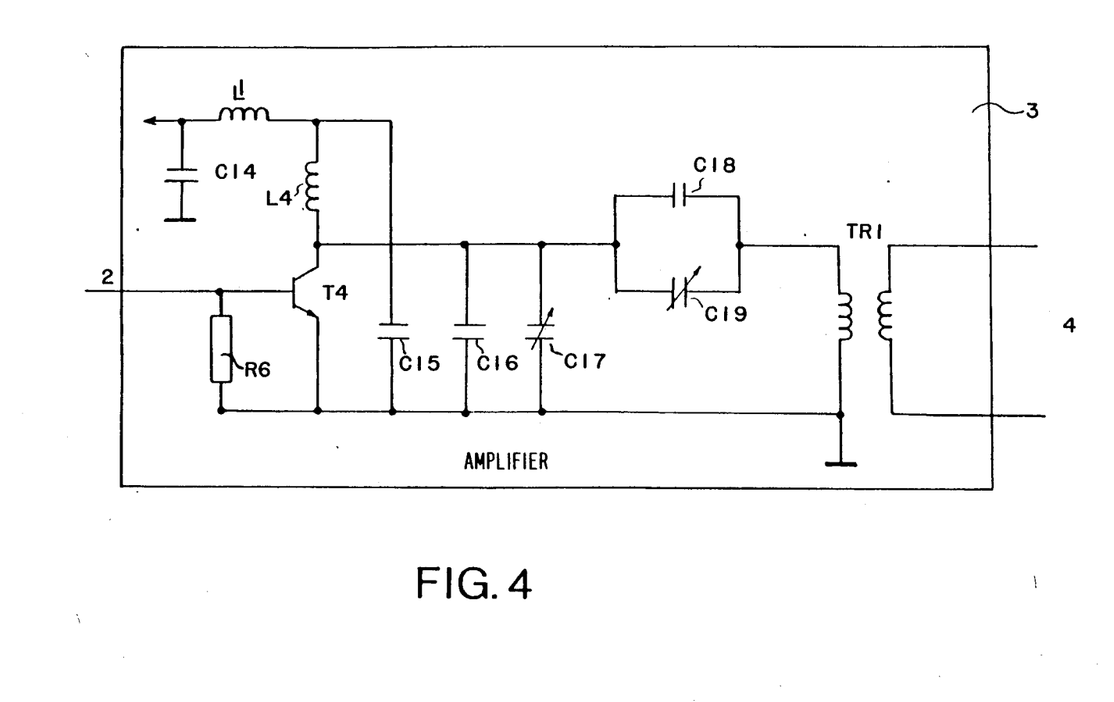
FIG. 4 is the schematic of the preamplifier.

The output of preamplifier 3, that is the collector of transistor T3, is connected by two capacitors C12 and C13 to the base of NPN transistor T4 of amplifier 4, FIG. 4. The base of transistor T4 is connected to ground by a resistor R6, its emitter is connected directly to ground and its collector is connected to a 24 V supply by an inductor L4 and a self-inductance choke $L^1$ having a terminal connected to the supply and connected to ground by a capacitor C14. Between the common point of inductors $L^1$ and L4, on one hand, and ground, on the other hand, there is a decoupling capacitor C15. The collector of transistors T4 is once again connected, on one hand, to ground by a fixed capacitor C16 in parallel with a variable capacitor C17, and, on the other hand, to a primary terminal of transformer TR1 by a parallel circuit comprising a fixed capacitor C18 and a variable capacitor C19. The other primary terminal of transformer TR1 is connected to ground. The transformer TR1 is, preferably, made up of a core of type 4C6 on which the secondary consists of 4 turns of a 3 mm wide copper plate and the primary consists of eight turns of 0.5 mm diameter copper wire.

The bias of transformer T4 provided by resistor R6 is such that the transistor operates in class C. The parallel tuning circuit is made up of inductance L4 and capacitors C16 and C17 while another transistor T4 collector charging circuit is made up of transformer TR1 whose leakage inductance is tuned by capacitors C18 and C19.

Figure 5:
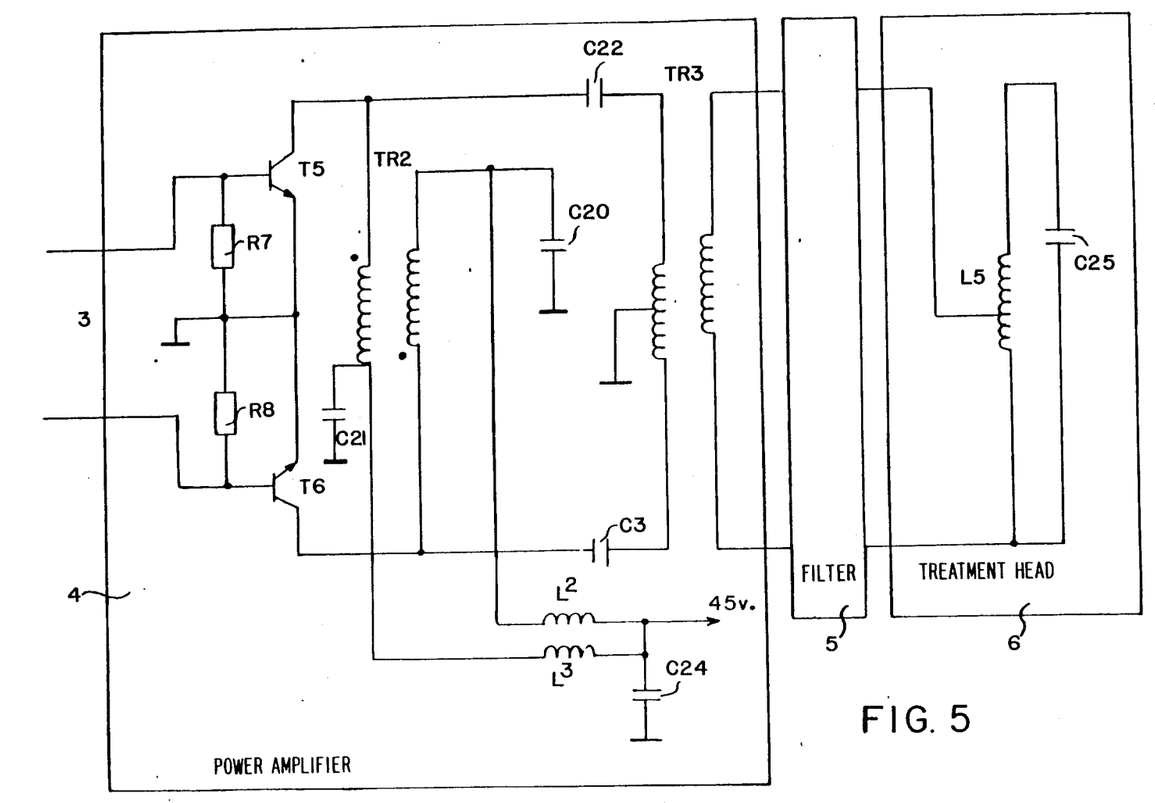
FIG. 5 is the schematic of the power amplifier.

In the power amplifier 4, FIG. 5, the secondary of transformer TR1 has its terminals respectively connected to the bases of the two NPN transistors T5 and T6, giving a push-pull arrangement. The bases of transistors T5 and T6 are respectively connected to ground by resistors R7 and R8. The emitters of transistors T5 and T6 are connected in parallel directly to ground. The collectors of transistors T5 and T6 are respectively connected to a 45 V source by two windings of a transformer TR2 in series with two self-inductive chokes $L^2$ and $L^3$. The 45 V source is decoupled from ground by a capacitor C24. The windings of transformer TR2 are made up of five turns of wires on a common ferrite bar. The common point between a winding on transformer TR2 and the self-inductor $L^2$ is connected to ground by a capacitor C20 while the other common point between the other winding and the self-inductor $L^3$ is connected to ground by a capacitor C21. The collectors of transistors T5 and T6 are again connected to the primary terminals of a transformer TR3 by coupling capacitors C22 and C23. The center point of the primary of TR2 is connected to ground.

One terminal of the secondary of transformer TR3 is connected to ground while the other is connected to the input of filter 5 whose output is connected to the treatment head which, from an electrical standpoint, behaves like an inductive winding L5 with an intermediate point connected to the output of the filter 5, one terminal is connected to ground and the other terminal is connected to one terminal of a capacitor C25 whose other electrode is connected to ground.

Figure 6:
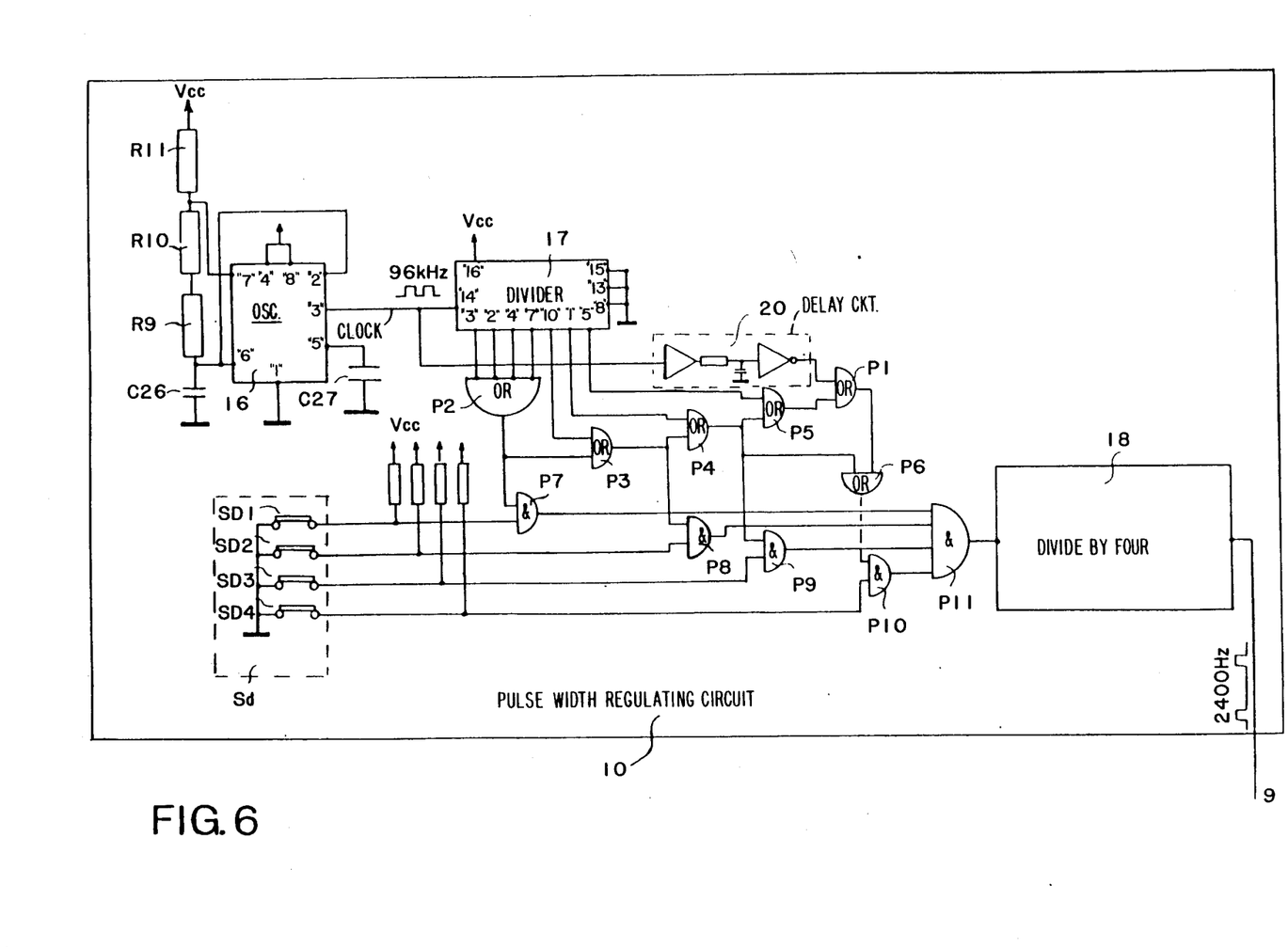
FIG. 6 is the schematic of the pulse width regulation circuit.

The pulse width regulating circuit 10, FIG. 6, comprises an oscillator 16, a divide by ten circuit 17, a divide by four circuit 18 and a given number of AND and OR gates.

The oscillator 16 is an integrated circuit 19 commercialized under the reference 555. The 555 circuit has its pin "6" connected to the Vcc supply by three resistors R9, R10 and R11 in series, which R10 being a variable resistor. Its pins "2" and "6" are connected to the point common to resistor R9 and capacitor C26. Its pins "6" and "5" are respectively decoupled to ground by capacitors C26 and C27. Its pins "4" and "8" are connected to the +Vcc supply. The values selected for the components are such that its pin "3" generates a pulsed signal at a frequency of 96 KHz. The tuning to a frequency of 96 KHz is achieved by selecting the values of the resistors R9 and R11 and the capacitor C26.

The output of oscillator 16 is, on one hand, is connected to the clock input of divider 17 and, on the other hand, through a delay circuit 20 to an input of an AND gate P1. The divider 17 is made up by a counter circuit commercialized under reference 4017. The input of the divider is connected to pin "14". Its pin "16" is connected to the +Vcc. Its pins "8", "13" and "15" are connected to ground.

The counter 17 operates as a divider by 10 and has its four outputs Q0 to Q3 connected to the input of an OR gate P2 whose output provides pulses of 40 microseconds duration with a repetition rate of 9.6 KHz. The output Q4 is connected to the input of an OR gate P3 whose second input is connected to the output of OR gate P2. The output Q5 is connected to one input of an OR gate P4 whose other input is connected to the output of gate P3. The output Q5 is connected to one input of an OR gate P5 whose other input is connected to the output of gate P4. The gates P3, P4 and P5 respectively generate pulses of 50, 60 and 70 microseconds duration. The output of gate P5 is connected to the second input of AND gate P1. The output of gate P1 is connected to one input of OR gate P6 whose other input is connected to the output of gate P4. Gate P6 generates impulses of 65 microseconds duration.

The outputs of gates P2, P3, P4 and P6 are respectively connected to the first inputs of AND gates P7, P8, P9 and P10. The second inputs of gates P7 to P10, respectively biased by resistors connected to the +Vcc supply, are respectively connected to activation contacts by touch keys SD1 to SD4 which upon opening put the corresponding second input to the Vcc level. The outputs of gates P7 to P10 are respectively connected to the four inputs of an OR gate P11 whose output is connected to the input of the divide by four circuit 18 which generates pulses at a frequency of 2400 Hz. The durations of the pulses generated by divider 18 vary between 40, 50, 60 or 65 microseconds depending on which key between SD1 to SD4 was activated. The set of keys SD1 to SD4 is grouped in box Sd of FIG. 1.

Figure 7:
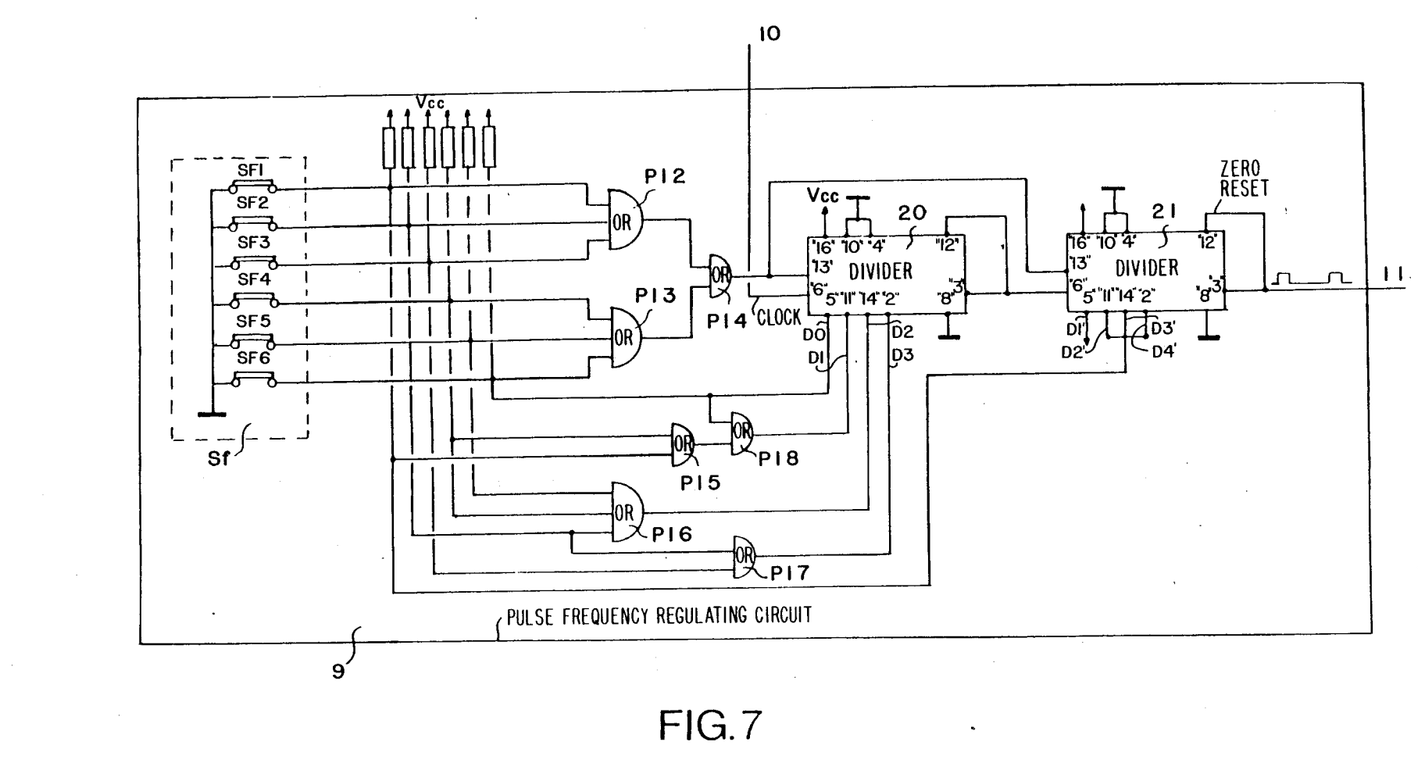
FIG. 7 is the schematic of the pulse frequency regulation circuit.

The pulse frequency regulating circuit 10, FIG. 7, comprises two dividers 20 and 21 arranged in cascade and a set of logic gates controlled by the contacts of keys Sf. The dividers 20 and 21 are counting circuits which are commercially available under reference 4526.

The divider 20 has its clocking input pin "6" connected to the output of the pulse duration regulating circuit 9 which feeds it with a train of impulses at a repetition rate of 2400 Hz. Its pin "3" carries its output signal which is connected, on one hand, to its own zero resetting pin "12" and, on the other hand, to the clocking input pin "6" of divider 21. Its pins "4", "8" and "10" are connected to ground and its pin "16" is connected to the +Vcc voltage source. Its divide ratio control pins "5", "11". "14" and "2" make up the inputs D0 to D3.

Figure 9:
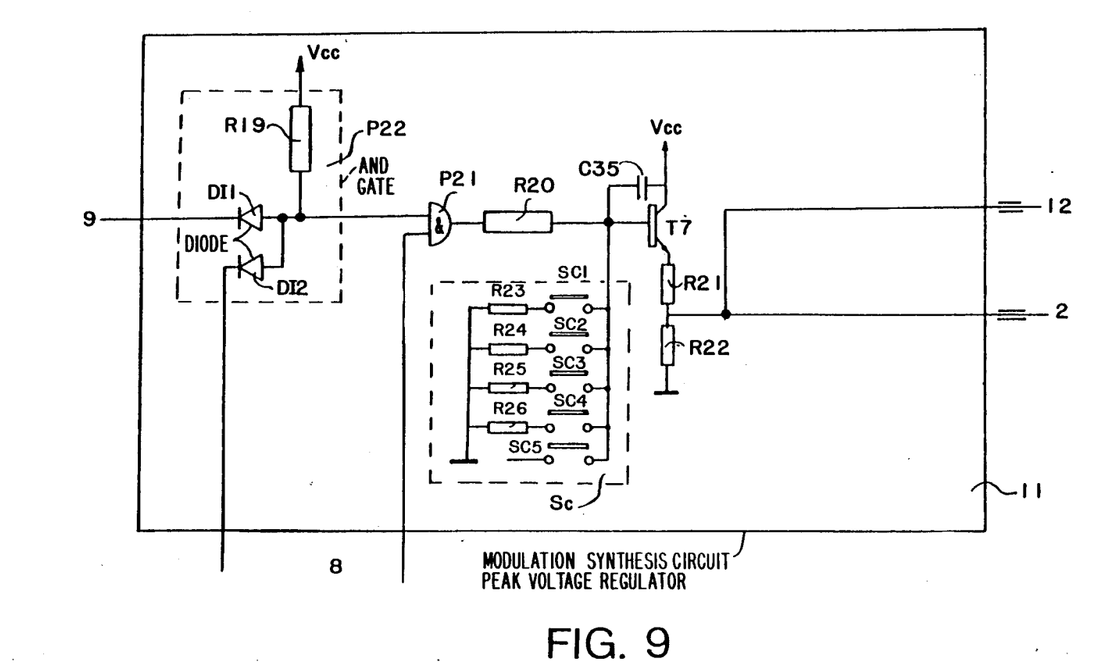
FIG. 9 is the schematic of the pulse modulation synthesis and impulse peak power regulation circuit.

The divider 21 has its pin "3" which carries the output signal connected, on one hand, to its zero resetting pin "12" and, on the other hand, to the cathode of diode DI1 (FIG. 9). Its pins "4", "8" and "10" are connected to ground and its pin "16" is connected to the +Vcc voltage source. Its divide ratio control pins "5", "11", "14" and "2" make up the inputs D'0 to D'3.

The key set Sf comprises six contact activation keys SF1 to SF6 which are intended to regulate the pulse repetition rate of divider 21 to 80, 200, 300, 400, 600 and 800 Hz respectively. One contact of keys SF1 to SF6 is connected to ground and the other is connected to the +Vcc voltage source through biasing resistors. The biased contacts of SF1 to SF3 and SF4 to SF6 are respectively connected to the inputs of OR gates P12 and P13 whose outputs are connected to the inputs of an OR gate P14 whose output is connected, in parallel, to the enable pin "13" of dividers 20 and 21.

In other respects, the biased contact key of SF1 is again connected, on one hand, to an input of an OR gate P15 and, on the other hand, in parallel to the inputs D'1 to D'3 of key divider 21. The biased contact of SF2 is again connected, on one hand, to one input of OR gate P16 and, on the other hand, to an input of OR gate P17. The biased contact of key SF3 is connected to the other input of OR gate P17. The biased contact of gate SF4 is connected to one input of P15 and to one input of gate P16. The biased contact of key SF5 is connected to the third input of key P16. Finally, the biased contact of key SF6 is connected, on one hand, to one input of OR gate P18 and, on the other hand, to the D0 input of divider 20. The output of gate P15 is connected to the second input of gate P18 whose output is connected to wire D1. The outputs of gate P16 and P17 are respectively connected to the inputs D2 and D3. The D'0 input of divider 21 is connected to the +Vcc voltage source.

The following truth table indicates the states of inputs D0 to D3 and D'0 to D'3 in terms of the activated keys SF1 to SF6.

| | Truth Table | | | | | | | | | | |
|---|---|---|---|---|---|---|---|---|---|---|---|
| | D0 | D1 | D2 | D3 | rd | D'0 | D'1 | D'2 | D'3 | rd' | Hz |
| SF1 | 0 | 1 | 0 | 0 | :2 | 1 | 1 | 1 | 1 | :15 | 80 |
| SF2 | 0 | 0 | 1 | 1 | :12 | 1 | 0 | 0 | 0 | :1 | 200 |
| SF3 | 0 | 0 | 0 | 1 | :8 | 1 | 0 | 0 | 0 | :1 | 300 |
| SF4 | 0 | 1 | 1 | 0 | :6 | 1 | 0 | 0 | 0 | :1 | 400 |
| SF5 | 0 | 0 | 1 | 0 | :4 | 1 | 0 | 0 | 0 | :1 | 600 |
| SF6 | 1 | 1 | 0 | 0 | :3 | 1 | 0 | 0 | 0 | :1 | 800 | where rd and rd' are the respective division ratios of dividers 20 and 21.

It is clear that pressing one of the keys SF1 to SF6 allows one to select the frequency of the pulse rate generated by circuit 10.

The operating time regulating circuit 8 (FIG. 8) comprises, in cascade, two monostables 22 and 23 made up of circuits of monostable type 555. Pin "2" of 22 is connected, on one hand, to the Vcc supply by a resistor R12 and, on the other hand, to one terminal of a coupling capacitor C28. The other end of capacitor C28 is connected to the output of an inverter I1 whose input is connected, on one hand, to ground by a capacitor C29 and, on the other hand, to the output of an AND gate P19 through a resistor R13. Pin "1" of divider 22 is at ground, pin "8" is at the Vcc supply voltage and pin "5" is connected to ground by a capacitor C30. An RC circuit comprising a capacitor C31, a fixed resistor R14 and a variable resistor R15 is provided between the Vcc supply and ground. The pins "6" and "7" are connected to the point common to resistor R14 and capacitor C31. Pin "3" is connected by a coupling capacitor C32 to pin "2" of monostable circuit 23.

Figure 8:
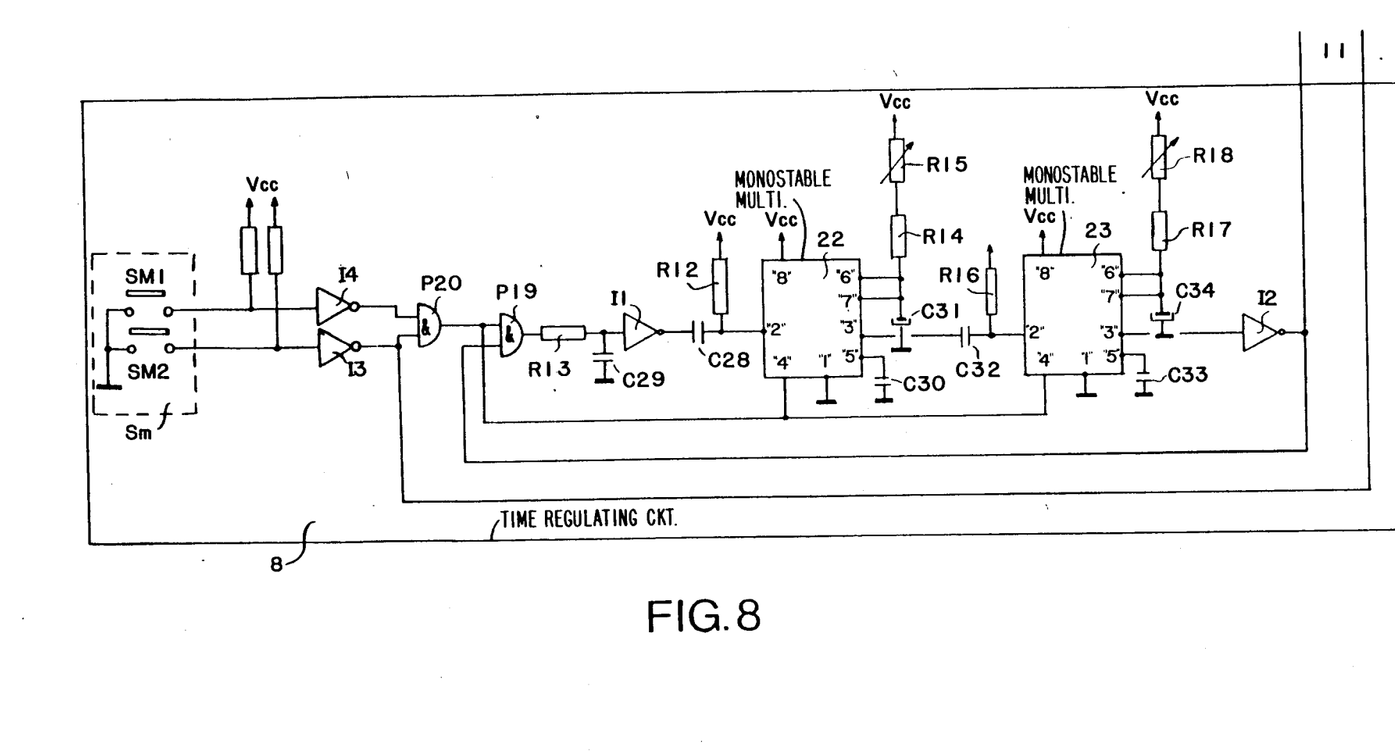
FIG. 8 is the schematic of the pulse burst duration regulator circuit.

The input pin "2" of circuit 23 is also connected to the supply voltage Vcc by a resistor R16. Its pin "1" is at ground, pin "8" is at the Vcc voltage and its pin "5" is connected to ground by a capacitor C33. A series circuit comprising a capacitor C34, a fixed resistor R17 and a variable resistor R18 is provided between the Vcc supply voltage and ground. The pins "6" and "7" are connected to the common point between capacitor C34 and resistor and R17. The output pin "3" is connected, on one hand, by an inverter I2 to the cathode of a diode DI2 (FIG. 9) and, on the other hand, to one input of AND gage P19.

The other input of gate P19 is connected to the output of AND gate P20. The output of gate P20 is also connected to pins "4" of 22 and 23. The two inputs of gate 20 are respectively connected, by inverters I3 and I4 to the "ON" contacts of keys SM1 and SM2 that make up the set Sm. In practice, the keys are arranged between ground and the Vcc supply by resistors. Finally, the inverter I3 which is tied to the contact SM1 is connected to one input of gate 21.

In practice, the contact SM1 is activated by a clocking apparatus which keeps it closed for the entire duration of the treatment; this duration being set on the clocking apparatus can vary between a few minutes to for example thirty minutes.

The contact SM2 is that of a single key.

The diodes DI1 and DI2 (FIG. 9) whose anodes are connected to the Vcc supply through resistor R19 make up AND gate P22. The cathodes of DI1 and DI2 make up the output of gate P22 and are connected to an input of AND gate P21.

When the instrument is powered, the output of inverter I2 (FIG. 8) is at a high level. Thus, gate P22 allows the train of impulses generated by circuit 10 to pass through. In other regards, when the clocking apparatus is activated, the corresponding input of gate 21 is set to a high level, such that the output of 21 generates the train of impulses during the whole time duration set on the clocking mechanism. When, furthermore, the rhythm key SM2 is pressed, the circuits 22 and 23 operate such that the output of inverter I1 remains at the high level during a time period T but transfers to the low level for a period T', this rhythm being cyclical. As a result gate 22 passes along the signal for a period T and blocks it for a period T'. For the sake of example, the RC networks 22 and 23 are selected such that T=4 minutes and T'=2 minutes.

More specifically, the locked on position of key SM2 allows AND gates P20 and P19 to pass along the signal. Thus the monostable 22 operates for four minutes by applying to its pin "3" a low level and monostable 23 is at rest. When, after four minutes, pin "3" goes to the high level, the transition is transmitted by capacitor C32 to monostable 23 which applies for two minutes a high level to its pin "3", which puts the output of invertor I2 at a low level. After these two minutes, the level of pin "3" changes such that I2 once again lets gate P19 pass along the signal and the transition is by C28 to 22. The cycle then starts over.

Figure 10:
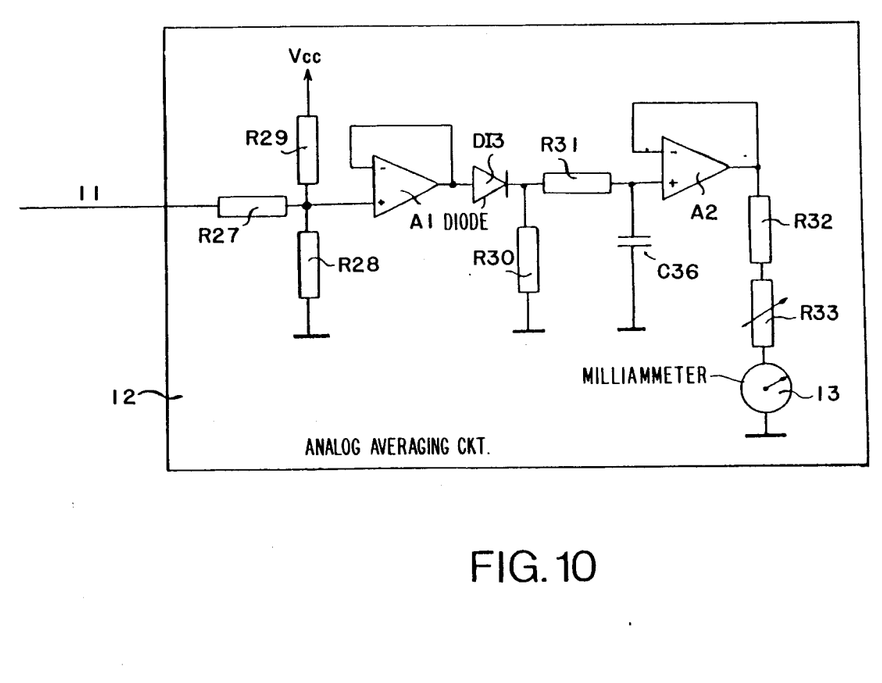
FIG. 10 is the schematic of the average power computation circuit.

In the peak voltage regulator circuit 11 (FIG. 9), the output of AND gate 21 is connected to the base of an NPN transistor T7 by a resistance R20. The collector of transistor T7 is connected directly to the Vcc supply. Its emitter is connected to ground by the series combination of resistors R21 and R22. Furthermore, the base of transistor T7 is connected to the first working contacts of the five keys SC1 to SC5. The second contacts of keys SC1 to SC4 are respectively connected to ground by four resistors R23 to R26. The second contact of SC5 is insulated. Finally, a capacitor C34 is connected between the base and the collector of transistor T7. The point common to resistors R21 and R22 constitutes the output of circuit I1. This point is connected, on one hand, by coaxial cable to the modulation input of modulator 2 (FIG. 1) and, on the other hand, to the input of analog averaging circuit 12 (FIG. 10).

In practice, when AND gate 21 (FIG. 9) allows the signal through, its output is at voltage Vcc, if key SC5 (or no key) is pressed, the transistor T7 being wired as an emitter follower, transmits the peak voltage. If one of the keys SC1 to SC 4 is pressed, the voltage at the base of transistor T7 takes on an intermediate value determined by resistor R20 and one of the resistors R23 to R25, and the transistor transmits a corresponding intermediate peak voltage. The capacitor C35 and the resistor R21 are set up to prevent oscillations in circuit 7.

The input of analog averaging circuit 12 is connected, by a resistor R27 to the non-inverting input of an operational amplifier A1. This non-inverting input is connected to ground by a resistor R28. The resistors R27 and R28 form a voltage divider. The non-inverting input is also connected to the Vcc supply by a resistor R29, which ensures that the voltage applied at amplifier A1 is positive. The output of amplifier A1 is connected, on one hand, to its non-inverting input and, on the other hand, to the anode of a diode DI3 whose cathode is connected, on one hand, to ground by a resistor R30 and, on the other hand, to the non-inverting input of an operational amplifier A2. The non-inverting input of amplifier A2 is also connected to ground by a capacitor C36. The resistors R30, R31 and the capacitor C36 restore the average voltage of the output signal of A1. The output of amplifier A2 is connected to its inverting input as well as to the input of a milliammeter 13 by the series combination of resistors R32 and R33.

Figure 11A:
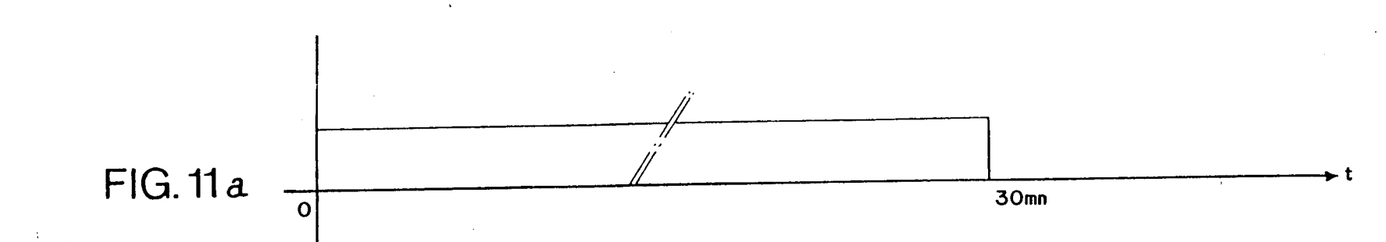
FIGS. 11A and 11B are diagrams illustrating the operation of circuit 8.

The timing diagram of FIG. 11a illustrates the mode of operation when only key SM2 is pressed. For a duration of, for example, thirty minutes, the head 6 transmits a high frequency signal at 27.125 MHz, at a peak power which is selected by the keys Sc. The HF signal is segmented into impulses whose duration is selected by keys Sd and whose frequency is selected by keys SF.

Figure 11B:
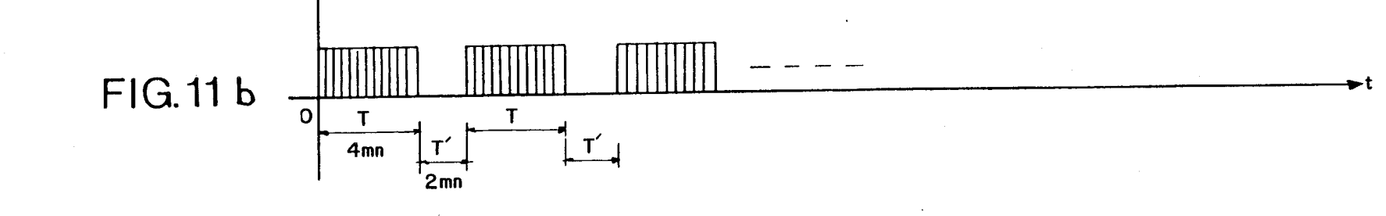

The timing diagram of FIG. 11b illustrates the rhythmic operating mode which is achieved when keys SM1 and SM2 are activated. In this case, the hand 6 (FIG. 1) transmits, as before, a pulsed HF signal, the parameters of which are selected as before. However, the transmission is rhythmic with an active period T and a rest period T', the duration of the treatment being determined, as previously, by the timer.

Figure 12:
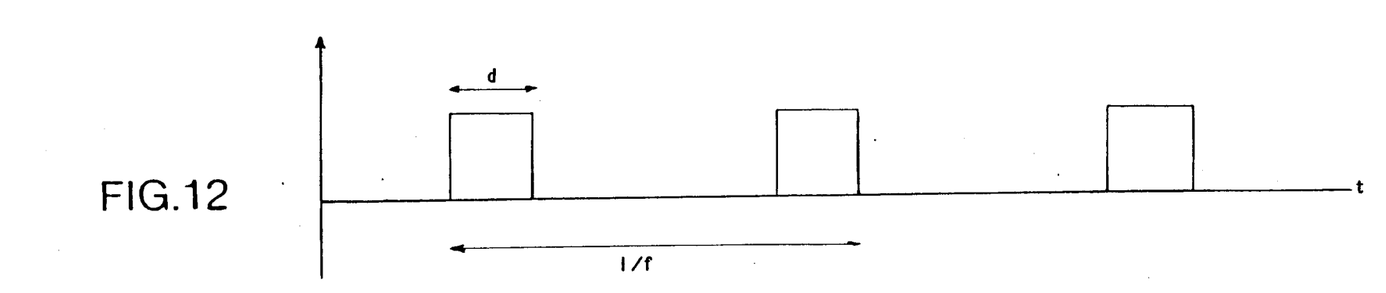
FIG. 12 is a diagram illustrating the operation of the circuits of FIGS. 6 and 7.

The timing diagram of FIG. 12 illustrates the shape of the signal at the output of transistor T7. The signal is made up of pulses of duration d determined by a key Sd, of a frequency determined by a key Sf and of amplitude determined by a key Sc.

The measuring instrument 13 enables the practitioner to read the average signal transmitted by the head and thus monitor the treatment carried out.

I claim:

1. A therapeutic non-thermal instrument comprising a treatment head having an excitation input, an open loop analog portion means coupled to drive said treatment head, said analog portion means generating and shaping a high frequency signal transmitted by the treatment head, a logic control means for generating time segment cuts and for regulating the peak amplitude of the high frequency signal; the analog portion means including, in cascade, a high frequency quartz crystal stabilized oscillator, a modulator having a modulation input, a preamplifier stage, a power amplifier stage, a bandpass filter having an output connected to said excitation input of the head; the logic control means generating a train of pulses which are applied to said modulating input of said modulator, said logic control means comprising a first digital circuit for regulating the duration of the pulses, a second digital circuit responsive to said first digital circuit for regulating the repetition rate of the pulses, a third digital circuit coupled to said modulation input and responsive to said second digital circuit for regulating the amplitude of the pulses, circuit means coupled to said third digital circuit for regulating a continuously rhythmic period of operation; a counter, the first digital circuit being a pulse width regulating circuit made up of a low frequency oscillator for generating a rectangular signal and having an output which is connected to the input of said counter, an array of OR gates coupled to the output of said counter for generating pulses of various widths in response to said rectangular signal, an array of AND gates having first inputs coupled to the outputs of said OR gates, a plurality of selection keys coupled to other inputs of said array of AND gates, and an output OR gate for uniting the outputs of said AND gates the output of said output OR gate constituting the output of the first digital circuit.

2. The instrument in accordance with claim 1, wherein the modulator includes a class C transistor amplifier tuned to the frequency of the high frequency oscillator, a supply voltage for the amplifier comprises a potential which is defined by said train of pulses applied from the logic control means to said modulating input of said modulator.

3. The instrument in accordance with claim 1 wherein a fixed ratio frequency divider is provided between the output OR gate uniting the outputs of said AND gates and the output of the first digital circuit.

4. The instrument in accordance with claim 1 and a set of keys coupled to said second digital circuit, the second digital circuit for regulating the pulse repetition rate being made up of a set of dividers having a signal input which is connected to the output of the first digital circuit, said dividers providing a divide ratio which is selected by said set of keys, the output of said dividers constituting the output of the second digital circuit.

5. The instrument in accordance with claim 1, wherein the third digital circuit for regulating the amplitude of the pulses is an emitter follower transistor stage, a voltage divider having an intermediate point, the base of said emitter follower transistor being connected to said intermediate point of said voltage divider which is connected between the output of the second digital circuit and a circuit ground, the voltage divider being made up of resistors controlled by a set of keys.

6. A therapeutic non-thermal instrument comprising a treatment head having an excitation input, an open loop analog portion means coupled to drive said treatment head, said analog portion means generating and shaping a high frequency signal transmitted by the treatment head, a logic control means for generating time segment cuts and for regulating the peak amplitude of the high frequency signal; the analog portion means including, in cascade, a high frequency quartz crystal stabilized oscillator, a modulator having a modulation input, a preamplifier stage, a power amplifier stage, a bandpass filter having an output connected to said excitation input of the head; the logic control means generating a train of pulses which are applied to said modulating input of said modulator, said logic control means comprising a first digital circuit for regulating the duration of the pulses, a second digital circuit responsive to said first digital circuit for regulating the repetition rate of the pulses, a third digital circuit responsive to said second digital circuit for regulating the amplitude of the pulses, the third digital circuit for regulating the amplitude of the pulses being an emitter follower transistor stage; a voltage divider having an intermediate point, the base of said emitter follower being connected to said intermediate point of said voltage divider which is connected between the output of the second digital circuit and a circuit ground, the voltage divider being made up of resistors controlled by a set of keys, and circuit means coupled to said third digital circuit for regulating a continuously rhythmic period of operation; a set of AND gates connected between the output of the first digital circuit and said voltage divider, said set of AND gates having one input which is marked by an enabling control signal during set time periods in response to the circuit means for regulating the continuously rhythmic period of operation.

7. The instrument in accordance with claim 6, wherein the modulator includes a class C transistor amplifier tuned to the frequency of the high frequency oscillator, a supply voltage for the amplifier comprises a potential which is defined by a train of pulses provided by the logic control means, part which provides said train of pulses.

8. A therapeutic non-thermal instrument comprising a treatment head having an excitation input, an open loop analog portion means coupled to drive said treatment head, said analog portion means generating and shaping a high frequency signal transmitted by the treatment head, a logic control means for generating time segment cuts and for regulating the peak amplitude of the high frequency signal; the analog portion means including, in cascade, a high frequency quartz crystal stabilized oscillator, a modulator having a modulation input, a preamplifier stage including a class C transistor amplifier having charging means comprised of a tuning circuit and a balancing transformer with a leakage inductance, capacitor means coupled to the transformer, said leakage inductance and the capacitance of said capacitors providing said tuning, a power amplifier stage, a bandpass filter having an output connected to said excitation input of the head; the logic control means generating a train of pulses which are applied to said modulating input of said modulator, said logic control means comprising a first digital circuit for regulating the duration of the pulses; a counter, the first digital circuit being a pulse width regulating circuit made up of a low frequency oscillator for generating a rectangular signal and having an output which is connected to the input of said counter, an array of OR gates coupled to the output of said counter for generating pulses of various widths in response to said rectangular signal, an array of AND gates having first inputs coupled to the outputs of said OR gates a plurality of selection keys coupled to other inputs of said array of AND gates, and an output OR gate for uniting the outputs of said AND gates the output of said output OR gate constituting the output of the first digital circuit; said second digital circuit being responsive to said first digital circuit for regulating the repetition rate of the pulses, said third digital circuit being couplled to said modulation input and responsive to said second digital circuit for regulating the amplitude of the pulses, and circuit means coupled to said third digital circuit for regulating a continuously rhythmic period of operation.

9. The instrument in accordance with claim 8, wherein the modulator includes a class C transistor amplifier tuned to the frequency of the high frequency oscillator, a supply voltage for the amplifier comprises a potential which is defined by a train of pulses provided by the logic control means, part which provides said train of pulses.

10. A therapeutic non-thermal instrument comprising a treatment head having an excitation input, an open loop analog portion means coupled to drive said treatment head, said analog portion means generating and shaping a high frequency signal transmitted by the treatment head, a logic control means for generating time segment cuts and for regulating the peak amplitude of the high frequency signal; the analog portion means including, in cascade, a quartz crystal, a high frequency oscillator including a transistor stabilized by said quartz crystal which is coupled thereto, the output of said oscillator being coupled to the input of a class C transistor amplifier, the output of the said amplifier being connected to the input of said modulator, a modulator having a modulation input, a preamplifier stage, a power amplifier stage, a bandpass filter having an output connected to said excitation input of the head; the logic control means generating a train of pulses which are applied to said modulating input of said modulator, said logic control means comprising a first digital circuit for regulating the duration of the pulses; a counter, the first digital circuit being a pulse width regulating circuit made up of a low frequency oscillator for generating a rectangular signal and having an output which is connected to the input of said counter, an array of OR gates coupled to the output of said counter for generating pulses of various widths in response to said rectangular signal, an array of AND gates having first inputs coupled to the outputs of said OR gates a plurality of selection keys coupled to other inputs of said array of AND gates, and an output OR gate for uniting the outputs of said AND gates the output of said output OR gate constituting the output of the first digital circuit; said second digital circuit being responsive to said first digital circuit for regulating the repetition rate of the pulses, said third digital circuit being coupled to said modulation input and responsive to said second digital circuit for regulating the amplitude of the pulses, and circuit means coupled to said third digital circuit for regulating a continuously rhythmic period of operation.

11. The instrument in accordance with claim 10, wherein the modulator includes a class C transistor amplifier tuned to the frequency of the high frequency oscillator, a supply voltage for the amplifier comprises a potential which is defined by a train of pulses provided by the logic control means, part which provides said train of pulses.

* * * * *